United States Patent [19]
Mas et al.

[11] Patent Number: 6,087,534
[45] Date of Patent: Jul. 11, 2000

[54] METHOD FOR SYNTHESIZING ARYL HYDRAZINE THROUGH REDUCTION OF A DIAZO COMPOUND DERIVATIVE

[75] Inventors: Jean-Manuel Mas, Millery; Christophe Rochin, Lyons, both of France

[73] Assignee: Rhodia Chimie, Courbevoie Cedex, France

[21] Appl. No.: 09/101,035

[22] PCT Filed: Dec. 27, 1996

[86] PCT No.: PCT/FR96/02089

§ 371 Date: Sep. 21, 1998

§ 102(e) Date: Sep. 21, 1998

[87] PCT Pub. No.: WO97/24316

PCT Pub. Date: Jul. 10, 1997

[30] Foreign Application Priority Data

Dec. 29, 1995 [FR] France ................................. 95 15711

[51] Int. Cl.⁷ .................................................. C07C 241/00
[52] U.S. Cl. .............................................................. 564/314
[58] Field of Search ................................................ 564/314

[56] References Cited

FOREIGN PATENT DOCUMENTS 39 01 705    7/1990    Germany .

OTHER PUBLICATIONS

Chemische Berichte, vol. 93, 1960, Weinheim DE, pp. 540–544, XP002014817, R. Huisgen et al, "Zum Mechanismus der Phenylhydrazinsynthese nach E. Fischer".

*Primary Examiner*—Paul J. Killos
*Attorney, Agent, or Firm*—Burns, Doane, Swecker & Mathis, L.L.P.

[57] ABSTRACT

The invention involves a procedure for synthesizing aryl hydrazine through reduction of a diazo derivative. The distinguishing feature of the method is that it involves at least the following step: c) bringing a diazo derivative into contact with a sulphite solution in which the pH level is at least 7. Applications: organic synthesis.

28 Claims, No Drawings

METHOD FOR SYNTHESIZING ARYL HYDRAZINE THROUGH REDUCTION OF A DIAZO COMPOUND DERIVATIVE

The present invention relates to a process for the synthesis of arylhydrazine or a derivative thereof by reduction of a diazo derivative. The invention relates more particularly to a bisulphite-type reduction.

The most direct route of access to hydrazines substituted with an aryl derivative is, in most cases, the diazotation of an aniline, followed by a reduction, generally a hydrogenation.

Besides being relatively expensive, this route has many difficulties, among which mention may be made of the often prohibitive number of steps and the formation of heavy by-products, resulting, ipso facto, in very mediocre overall yield and purity. On top of all this, the reduction techniques give erratic results, depending on the substituents on the rings. The problem is particularly pronounced in the case of electron-poor aromatic rings.

Thus, in the course of the study which led to the present invention, it has been shown that the most standard technique for reducing "diazo" compounds, i.e. the use of tin, gives results which, at best, can only be described as mediocre.

Accordingly, one of the aims of the present invention is to provide a process which makes it possible to obtain arylhydrazine from a diazo derivative.

Another aim of the present invention is to provide a process which is suitable for electron-poor or moderately electron-poor rings.

Another aim of the present invention is to provide a process which allows a good yield.

Another aim of the present invention is to provide a process which allows the one-step production of arylhydrazines which can readily be purified or which can even be obtained directly in high purity.

These aims and others which will become apparent hereinbelow are achieved by means of a process for reducing a diazo derivative, this process including at least the following step:

c) placing the diazo derivative in contact with a sulphite solution whose pH is at least equal to 7.

The reason for this is that the use of sulphite has proved to be particularly advantageous as a reducing agent provided that it is at a sufficiently basic pH. This is particularly surprising since the reduction reaction requires the presence of acidic ions.

Advantageously, in order to avoid the presence of a coloured product which would impair the purity and colour of the hydrazine, and thus in order to avoid a rigorous purification step, it is desirable to work at a pH of between 7.2 and 11, preferably between 7.5 and 10.

In order to avoid the presence of tars and heavy products, it is preferable for the temperature at which step c) is carried out to be at most equal to 100° C., advantageously to 50° C.

Although this cannot be fully explained, the best results are obtained when the pH of the sulphite/bisulphite solution is buffered with a nitrogenous base (such as amines, including anilines) whose pKb is between 6 and 11; preferably, the pH is buffered with a nitrogenous base whose pKb is between 7 and 10.

For economic reasons, the said nitrogenous base is aqueous ammonia.

According to a particularly advantageous embodiment of the present invention, step c) is carried out by addition of the said diazo derivative to an initial charge of reductive bisulphite solution.

It is desirable for the pH to be adjusted during step c) such that it is always close to a preselected value and above 7 and below 11, advantageously below 10.

The process advantageously also includes a step a) of synthesis of the diazo derivative, in particular in order to avoid having to insert the diazo derivative to be reduced.

This step a) of synthesis of the diazo derivative is generally carried out by the action of a nitrite, advantageously an alkyl or metal nitrite, on an aniline.

Advantageously, the said nitrite is an alkaline nitrite.

In general, the said diazo derivative is a diazonium salt.

The results are more predictable if the aromatic ring bearing the diazo function is a benzene ring.

The process is particularly advantageous when the said benzene ring, not taking the diazo function into account, has substituents such that it is electron-poor overall, or, preferably and, when the benzene ring, not taking the diazo function into account, is electron-poor due to an inductive effect by at least one electron-withdrawing function. It is preferred when the two conditions are present together.

It is desirable for the said benzene ring not to have any mesomeric-effect electron-withdrawing substituents.

When the ring bears substituents, the electron-richness of the ring can be evaluated with the aid of the $\delta_p$ constants known as the "Hammett" constants. Thus, the sum of the Hammett constants for the substituents on the said benzene ring, not taking the diazo function into account, is between 0.1 and 0.7; advantageously between 0.1 and 0.5; preferably between 0.1 and 0.35.

For further details regarding the Hammett constants, reference may be made to the third edition of the book by Professor Jerry March *Advanced Organic Chemistry* (pages 242 to 250) published by John Wiley and Sons.

When the benzene ring has only one electron-withdrawing substituent, the electron-withdrawing substituent does so mainly by means of an inductive effect. In addition, it is desirable for the said electron-withdrawing substituent to be in a position ortho or para to the diazo function.

These electron-withdrawing substituents are advantageously chosen from light halogens (chlorine and/or preferably fluorine), nitrite and perhaloalkyls.

To avoid the degradation of the diazo derivative in the reaction mixture, and thus to avoid having to separate the "diazo" derivative from the reaction mixture from which it is obtained, it is desirable for the process also to include a step b) of reduction of the nitrite content.

It is also possible to go directly from step a) to step c) provided that the insertion is avoided and that the reaction mixture is used quickly after step a). This is the case in continuous or semi-continuous processes.

Advantageously, the said step b) of reducing the nitrite content is carried out by placing the reaction mixture obtained in step a) in contact with an agent for reducing the nitrite function, advantageously an amide acid, preferably sulphamic acid and/or a derivative thereof.

To complete the process, and if the hydrazine derivative obtained in step c) cannot be used as it is, the process also includes a step d) of hydrolysis of the sulphone derivative obtained in step c).

This step d) of hydrolysis of the sulphone derivative is advantageously carried out in acidic medium, preferably in hydrochloric acid medium. This step d) of hydrolysis of the sulphone derivative is carried out at a temperature of between 20° C. and 70° C., preferably between 40 and 60° C.

The non-limiting examples which follow illustrate the invention.

PREPARATION OF 2-FLUOROPHENYLHYDRAZINE

SALIFICATION 400 g of distilled water are placed in a 6-liter jacketed reactor placed under an inert atmosphere of nitrogen and equipped with a mechanical stirrer, a condenser, a dropping funnel and a thermometer probe, and 470 ml of aqueous 32.5% hydrochloric acid solution are then added over about 30 minutes.

The temperature of the solution is brought to 80° C. and 224 g (2 mol) of 2-fluoroaniline (99% pure) are then added over one hour. The reaction mixture is maintained for ½ hour under these conditions.

DIAZOTIZATION

The 2-fluoroaniline hydrochloride solution is cooled to 0° C. The hydrochloride precipitates and a stirrable white broth is obtained.

363 g of aqueous 40% sodium nitrite solution are then added over 2 h 30 min and so as not to exceed 3° C. in the broth. The medium becomes homogeneous and turns an orange-red colour.

After completing for 30 minutes, 97 g of aqueous 12.5% sulphamic acid solution are added very slowly, in order to destroy the excess sodium nitrite. The evolution of nitrogen results in the formation of a foam. After completion for ½ hour, the medium is drawn down.

REDUCTION

After preparing the reductive solution by addition of 285 g of 28% aqueous ammonia solution to 1547 g of aqueous 40% sodium bisulphite solution over ½ hour and returning the medium to a temperature of 25° C., the diazo solution is added over 2 hours. The reaction medium is then heated at 50° C. for 30 minutes.

HYDROLYSIS

After this period, 1123 g of aqueous 30% hydrochloric acid solution are added over about 3 hours. The homogeneous orange-yellow medium is maintained at 50° C. for 30 minutes.

Note: It is possible at this stage to carry out an extraction with toluene in order to remove certain heavy products which might have been formed.

NEUTRALIZATION

The base hydrazine is then released by slow addition of 1250 ml of aqueous 30.5% sodium hydroxide solution. The medium is then extracted with 450 ml of toluene, followed by 2×300 ml of toluene. The organic phases are combined.

DESOLVATATION

The desolvatation is carried out by stripping with nitrogen (70° C. at 10 mm Hg) after partial distillation of the toluene, i.e. by distillation on "Luwa" type apparatus, working at 70° C. under 5 mm Hg.

241 g of crude product assaying at 96.1% by HPLC analysis are thus obtained.

Yield of isolated product=92%.

What is claimed is:

1. Process for the synthesis of arylhydrazine by reduction of a diazo derivative, comprising:
   c) placing the diazo derivative in contact with a sulphite solution whose pH is at least equal to 7.

2. Process according to claim 1, wherein said pH is between 7.2 and 11.

3. Process according to claim 1, wherein said pH is between 7.5 and 10.

4. Process according to claim 1, wherein the temperature at which step c) is carried out is at most equal to 100° C.

5. Process according to claim 4, wherein said temperature is at most equal to 50° C.

6. Process according to claim 1, wherein the pH of the sulphite solution is buffered with a nitrogenous base whose pKb is between 6 and 11.

7. Process according to claim 1, wherein the pH of the sulphite solution is buffered with a nitrogenous base whose pKb is between 7 and 10.

8. Process according to claim 7, wherein said nitrogenous base is aqueous ammonia.

9. Process according to claim 1, wherein step c) is carried out by addition of the said diazo derivative to an initial charge of reductive bisulphite solution.

10. Process according to claim 1, wherein during step c), the pH is adjusted such that it is always close to a value above 7 and below 11, advantageously below 10.

11. Process according to claim 1, further comprising a step a) of synthesis of the diazo derivative.

12. Process according to claim 11, wherein said step a) of synthesis of the diazo derivative is carried out by the action of a nitrite on an aniline.

13. Process according to claim 12, wherein said nitrite is an alkaline nitrite.

14. Process according to claim 1, wherein said diazo derivative is a diazonium salt.

15. Process according to claim 1, wherein the aromatic ring bearing the diazo function is a benzene ring.

16. Process according to claim 15, wherein said benzene ring is, not taking the diazo function into account, electron-poor owing to an inductive effect by at least one electron-withdrawing function.

17. Process according to claim 15, wherein said benzene ring, not taking the diazo function into account, has substituents such that it is electron-poor overall.

18. Process according to claim 15, wherein said benzene ring has no mesomeric-effect electron-withdrawing substituents.

19. Process according to claim 15, wherein the sum of the Hammett constants of the substituents on the said benzene ring is between 0.1 and 0.7.

20. Process according to claim 15, wherein said benzene ring has only one electron-withdrawing substituent, said electron-withdrawing substituent being electron-withdrawing by means of an inductive effect.

21. Process according to claim 15, wherein said electron-withdrawing substituent is located in a position ortho or para to the diazo function.

22. Process according to claim 1, wherein the electron-withdrawing substituents are chosen from light halogens, nitrite and perhaloalkyls.

23. Process according to claim 11, further comprising a step b) of reduction of the nitrite content.

24. Process according to claim 23, wherein said step b) of reduction of the nitrite content is carried out by placing the reaction mixture obtained in step a) in contact with a reducing agent for the nitrite function.

25. Process according to claim 1, further comprising a step d) of hydrolysis of the sulphone derivative obtained in step c).

26. Process according to claim 25, wherein step d) of hydrolysis of the sulphone derivative is carried out in acidic medium.

27. Process according to claim 25, characterized in that the step d) of hydrolysis of the sulphone derivative is carried out at a temperature of between 20° C. and 70° C.

28. Process for the synthesis of arylhydrazine by reduction of a diazo derivative, comprising:
   c) placing the diazo derivative in contact with a sulphite solution whose pH is at least equal to 7;

wherein the pH of the sulphite solution is buffered with a nitrogenous base whose pKb is between 6 and 11.

* * * * *